US011622456B2

(12) United States Patent
Stalter et al.

(10) Patent No.: US 11,622,456 B2
(45) Date of Patent: *Apr. 4, 2023

(54) METHODS AND SYSTEMS FOR A CABLE MANAGEMENT SYSTEM

(71) Applicant: GE Precision Healthcare LLC, Milwaukee, WI (US)

(72) Inventors: Ross Christopher Stalter, Hartland, WI (US); William Zang, Grafton, WI (US); Del France, San Rafael, CA (US)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/446,069

(22) Filed: Aug. 26, 2021

(65) Prior Publication Data

US 2021/0392766 A1 Dec. 16, 2021

Related U.S. Application Data (63) Continuation of application No. 16/591,515, filed on Oct. 2, 2019, now Pat. No. 11,153,981.

(51) Int. Cl.
*H05K 5/02* (2006.01)
*H05K 5/00* (2006.01)
*A61B 90/00* (2016.01)

(52) U.S. Cl.
CPC ......... *H05K 5/0217* (2013.01); *H05K 5/0017* (2013.01); *A61B 90/37* (2016.02); *A61B 2090/372* (2016.02)

(58) Field of Classification Search
CPC .... H05K 5/0217; H05K 5/0017; A61B 90/37; A61B 2090/372

USPC ...... 248/49, 592, 674, 659, 693, 309.1, 548; 174/68.1

See application file for complete search history.

(56) References Cited

U.S. PATENT DOCUMENTS

| 3,181,419 | A1 | 5/2012 | diGirolamo | |
|---|---|---|---|---|
| 8,181,419 | B1* | 5/2012 | diGirolamo | E04B 2/768 52/712 |
| 9,385,513 | B2 | 7/2016 | Jones | |
| 11,153,981 | B2* | 10/2021 | Stalter | H05K 5/0017 |
| 2019/0380681 | A1* | 12/2019 | Meurer | A61B 8/4427 |
| 2020/0403390 | A1* | 12/2020 | Jette | H02S 40/30 |
| 2021/0085415 | A1* | 3/2021 | Stalter | A61B 8/4405 |

FOREIGN PATENT DOCUMENTS

CN 102742104 A 10/2012

OTHER PUBLICATIONS

CN application 202011002603.7 filed Sep. 22, 2020—Office Action dated Nov. 29, 2021; 8 pages.

* cited by examiner

Primary Examiner — Todd M Epps
(74) Attorney, Agent, or Firm — McCoy Russell LLP (57) ABSTRACT

Various methods and systems are provided for a cable management device. In one example, the cable management device has a planar base with a plurality of mounting holes, a first wing framing a first slot positioned along a first side of the base, and a second wing framing a second slot along a second side of the base. The wings may flex from a first configuration to a second configuration in response to a contact force.

20 Claims, 7 Drawing Sheets

METHODS AND SYSTEMS FOR A CABLE MANAGEMENT SYSTEM

CROSS REFERENCE TO RELATED APPLICATIONS

The present application is a continuation of U.S. Non-Provisional patent application Ser. No. 16/591,515, entitled "METHODS AND SYSTEMS FOR A CABLE MANAGEMENT SYSTEM", and filed on Oct. 2, 2019. The entire contents of the above-listed application are hereby incorporated by reference for all purposes.

FIELD

Embodiments of the subject matter disclosed herein relate to a cable management system for a medical device.

BACKGROUND

A medical system, e.g., a diagnostic system or an imaging systems, etc., may include a variety of accessory devices attached to various regions of the medical system. The accessory devices are electrically coupled to the medical system via cables which may be hung or tied to supporting structures for the accessory devices. However, hanging or tying the cables may cause binding and rubbing of the cables, particularly when the accessory devices are frequently relocated or configured to be mobile. Thus a cable management system that allows the cables to move freely while circumventing tangling of the cables is desirable.

BRIEF DESCRIPTION

In one embodiment, a cable management device includes a planar base with a plurality of mounting holes, a first wing framing a first slot positioned along a first side of the base and a second wing framing a second slot positioned along a second side of the base, opposite of the first side, and wherein the first wing and the second wing are configured to flex from a first configuration to a second configuration in response to a contact force exerted on the wings. In this way, the cable management device may be used to maintain one or more cables in an arrangement that reduces tangling and chafing of the cables.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3:
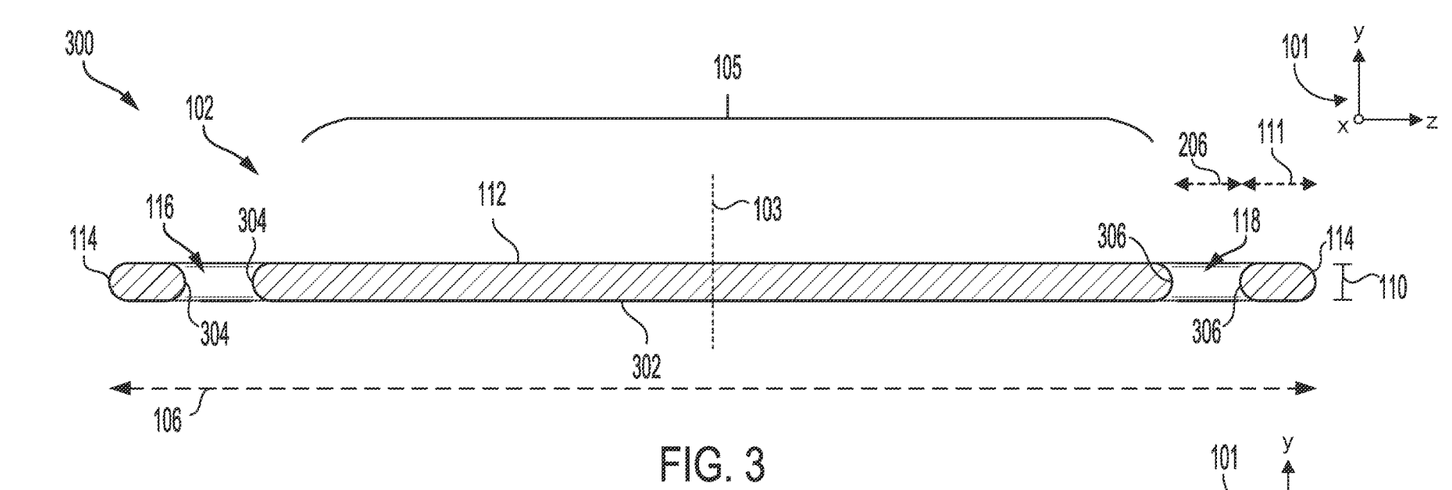
FIG. 3 shows a first cross-section of the flexible cable management device of FIGS. 1-2 in the first configuration.
Figure 4:
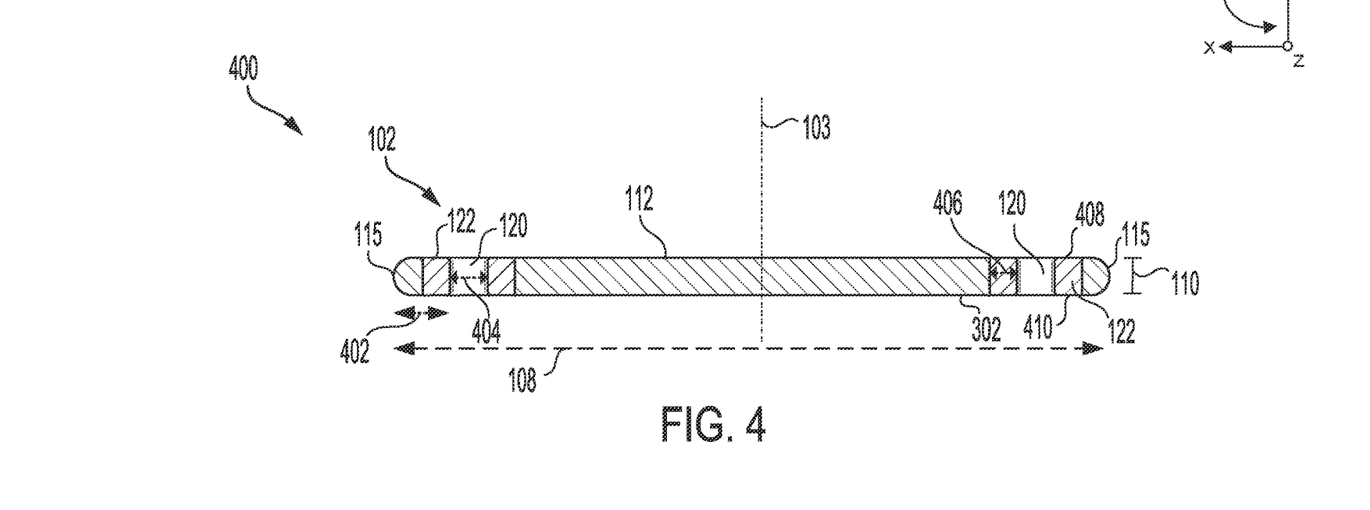
FIG. 4 shows a second cross-section of the flexible cable management device of FIGS. 1-3 in the first configuration.
Figure 5:
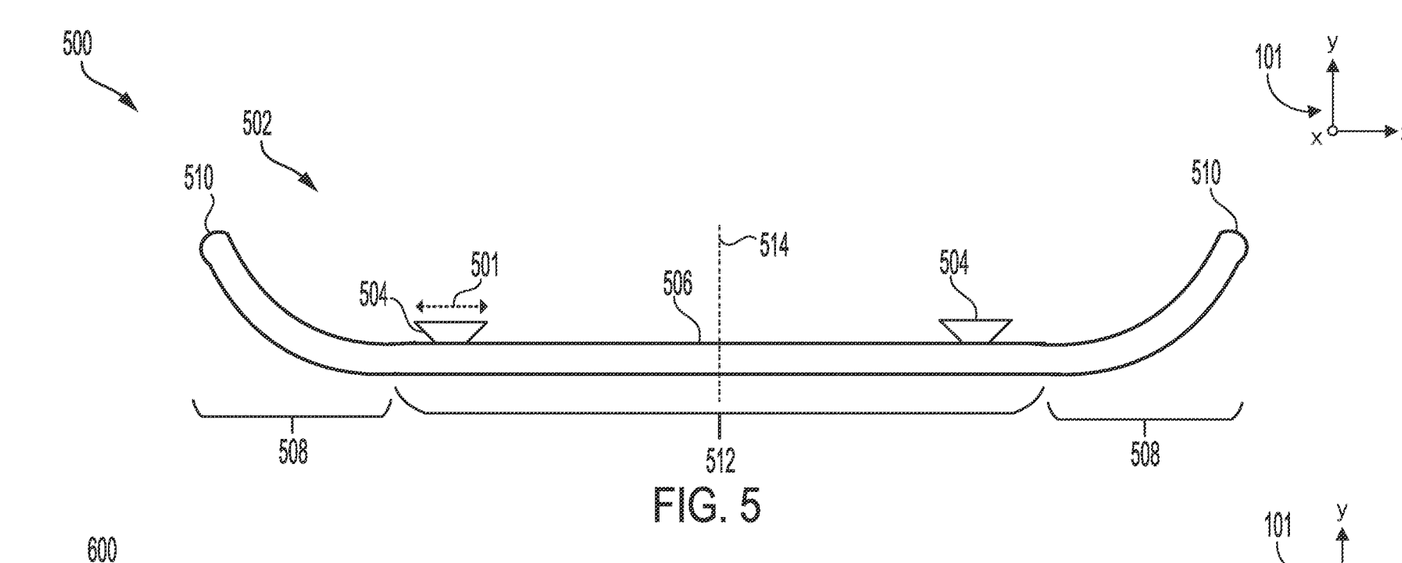
FIG. 5 shows a profile view of a flexible cable management device in a second configuration.
Figure 6:
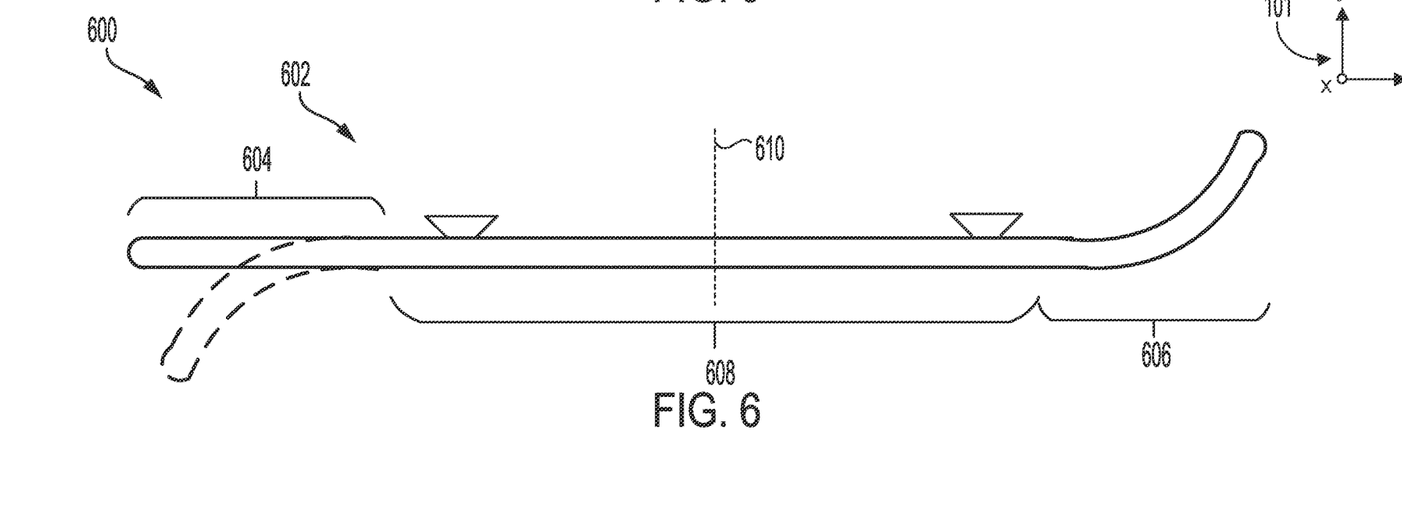
FIG. 6 shows a profile view of a flexible cable management device in a third configuration.
Figure 7:
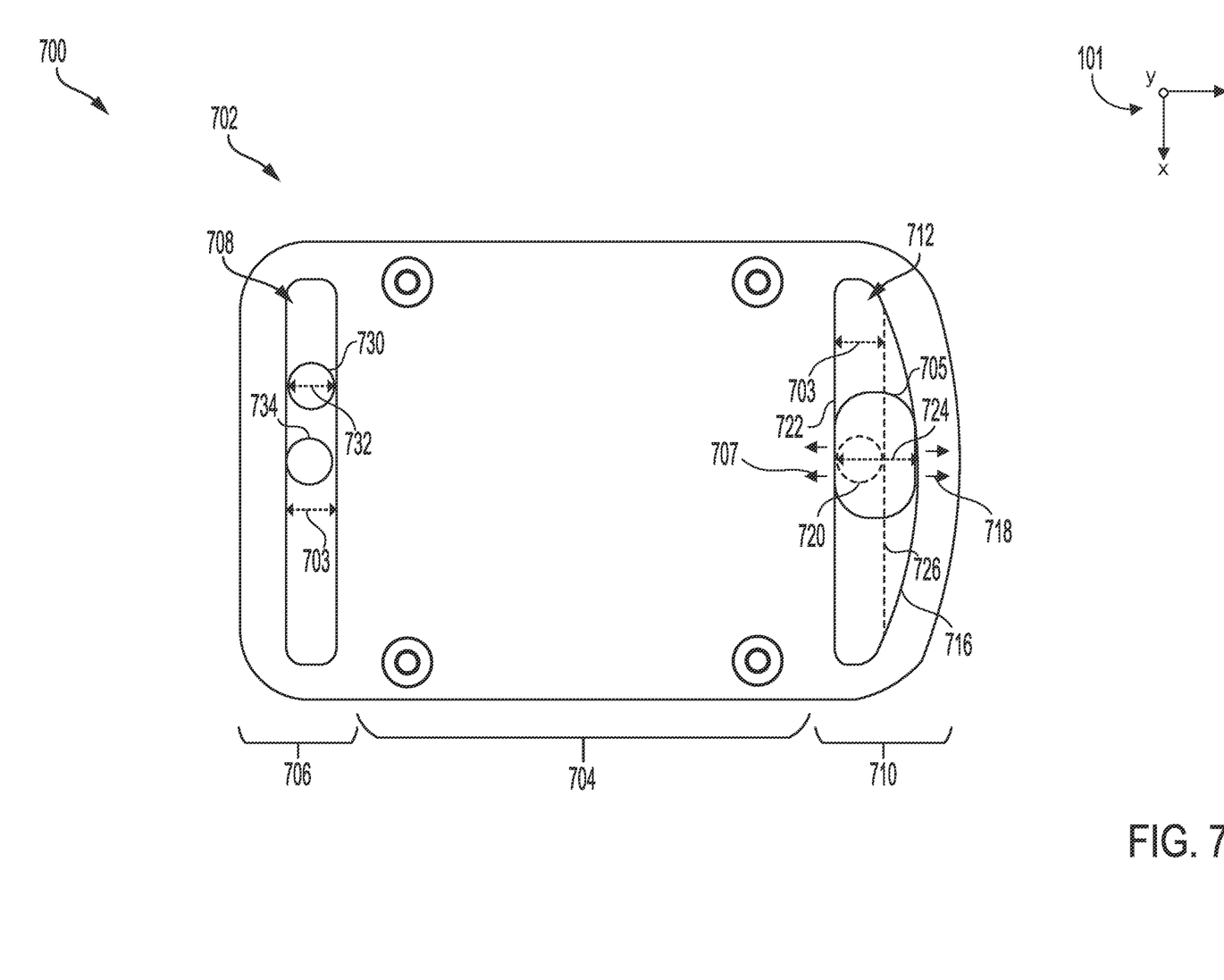
FIG. 7 shows a top view of a flexible cable management device in a fourth configuration.
Figure 8:
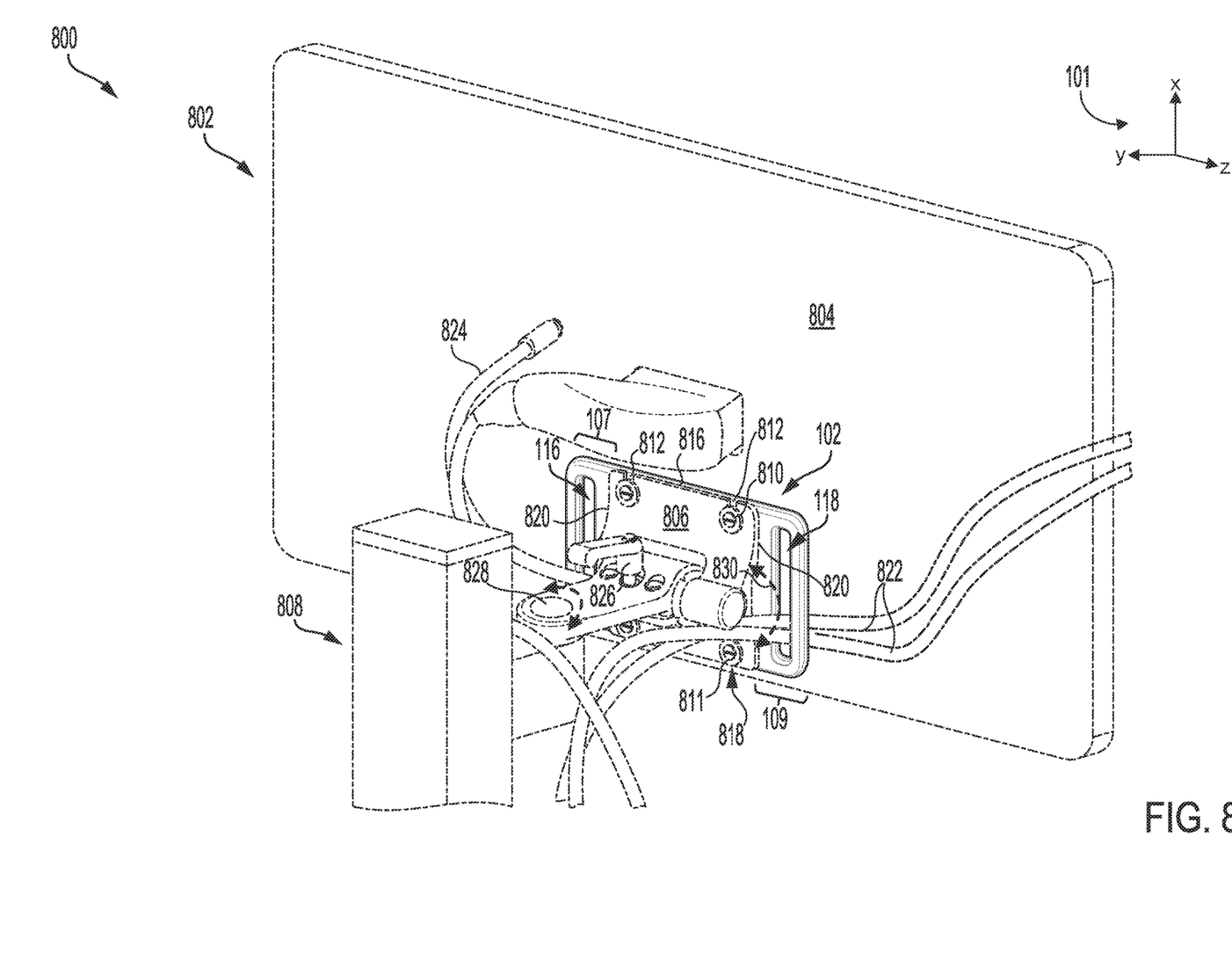
FIG. 8 shows the flexible cable management device of FIGS. 1-4 coupled to a medical imaging system.
Figure 9:
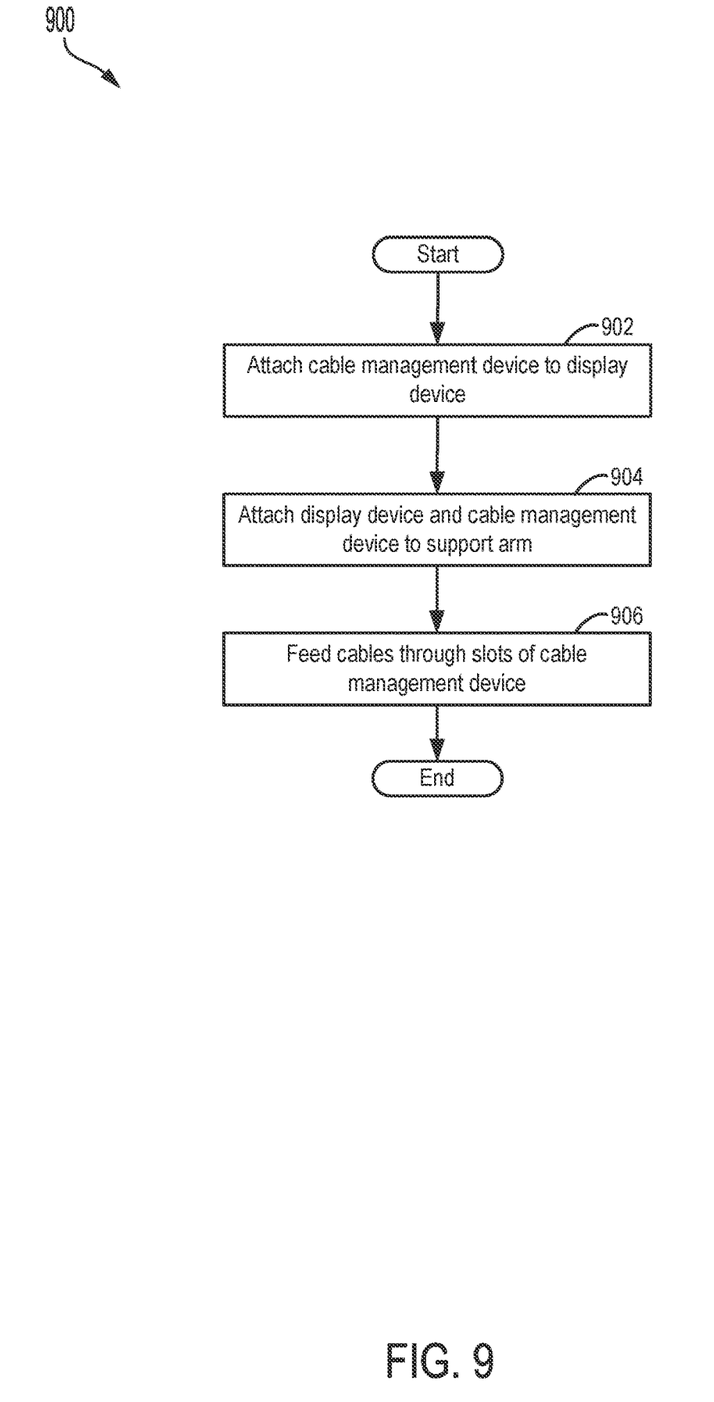
FIG. 9 shows an example of a method for a flexible cable management device.

The following description relates to various embodiments of a cable management system. The cable management system may include a flexible cable management device that includes windows or slots through which cables may be passed. An example of the cable management device is shown in FIGS. 1-4 where the cable management device is in a first, planar configuration. Alternatively, the cable management device may be in a second configuration, as shown in FIG. 5, a third configuration, as shown in FIG. 6, and/or a fourth configuration, as shown in FIG. 7. The cable management device may be adjusted to any of the first, second, and third configurations when coupled to a medical display system, as depicted in FIG. 8. A method for organizing cables of a medical system via the cable management device is shown in FIG. 9.

FIGS. 1-8 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

A medical system may include more than one cable coupling various accessory devices to the medical system. In one example, the medical system may include a display unit configured with a VESA mount. A cable of the display unit, as well as other cables connected to devices arranged adjacent to the display unit or coupled to display unit, e.g., probes, input devices, cameras, etc., may extend along a rear side of the display unit. The cables may be placed so that the cables do not interfere with operation of the medical system by draping or hanging the cables over external, adjacent structures. In other examples, the cables may be bundled together to mitigate spreading and tangling of the cables.

However, when the cables are draped over a rigid external structure, such as an arm supporting a display device of the medical system, hard edges of the external structure may chafe the cables. As well, when the cables are bundled using a rigid device, the cables may rub and crimp when twisting or rotation of the cables is demanded, leading to degradation of the cables. Alternatively, if the cable is secured too loosely, the cables may become dislodged and entangled, disrupting a workflow of an operator. Such issues may be at least partially addressed by a flexible, elastic, rebounding panel that may be coupled to a mount of the display unit. The panel may be a cable management device, configured to retain a position of the cables at a rear side of the display unit, near mobile joints of a support arm holding the display unit.

A material of the flexible cable management device may provide a balance between enough rigidity to retain a desired positioning of the cables when in a first configuration while having an elasticity that allows the cable management device to flex and deform to a second configuration to allow cable plugs to be passed through. Once the cable plugs are passed, the cable management device may rebound to the first configuration and remain in the first configuration even during shifting of the cables supported by the cable management device. By adapting the cable management device with a base that may be directly coupled to the mount of the display unit and peripheral slots through which cables may be threaded, the cables may be secured to the display unit while allowing the cables to move. An example of a cable management device 102 is depicted in FIGS. 1-6 from various views. The cable management device 102 is shown in a first configuration in FIGS. 1-6.

Figure 1:
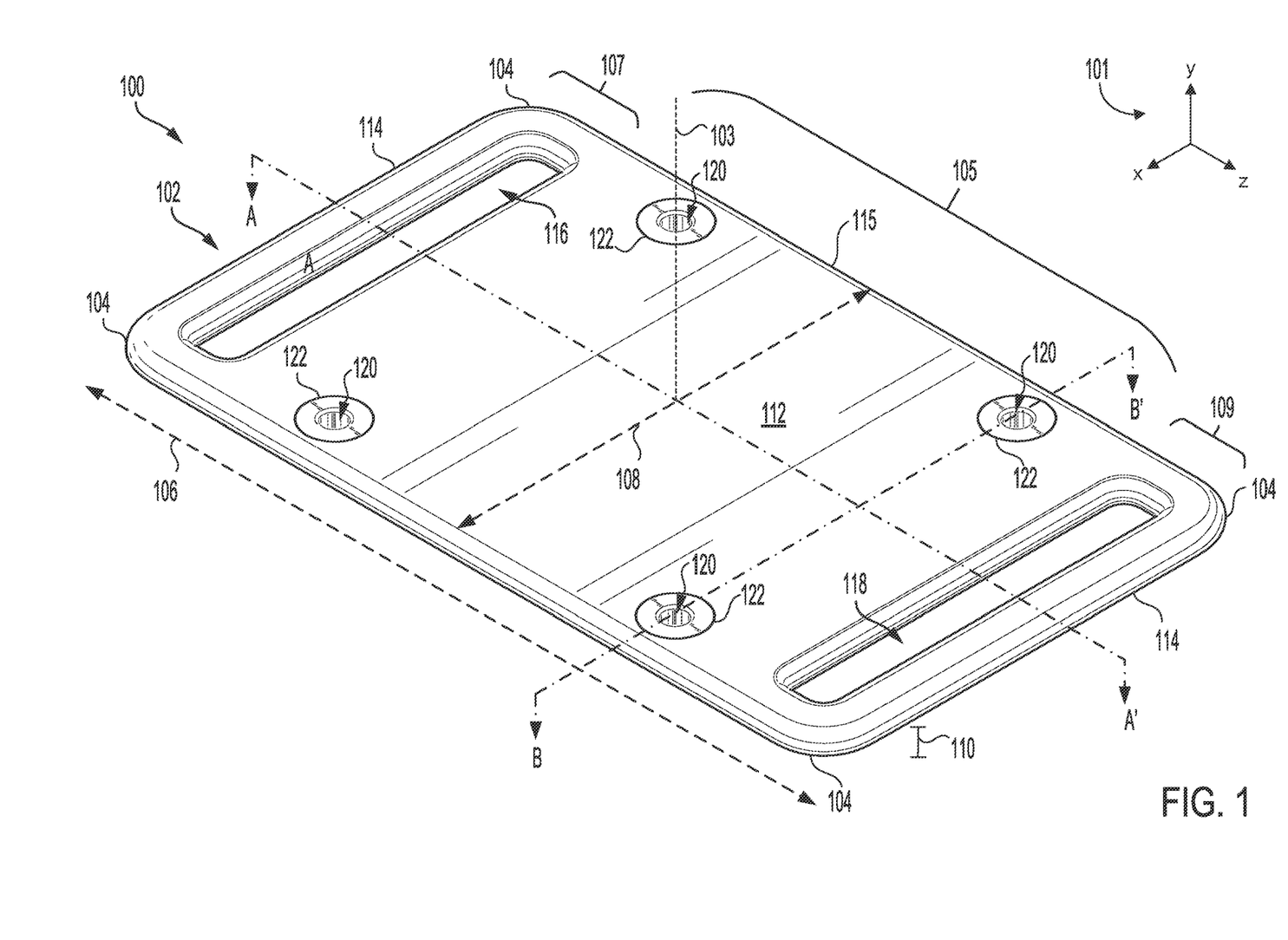
FIG. 1 shows a perspective view of an example of a flexible cable management device in a first configuration.

A perspective view 100 of the cable management device 102 is illustrated in FIG. 1. A set of reference axes 101 are provided for comparison between views shown, indicating a y-axis, an x-axis, and a z-axis. In one example, the cable management device 102 may a rectangular plate with curved corners 104. A length 106 of the cable management device 102, defined along the z-axis, is greater than a width 108 of the cable management device 102, defined along the x-axis, and both the length 106 and the width 108 are greater than a thickness 110 of the cable management device 102, defined along the y-axis. The thickness 110 may be uniform along both the length 106 and the width 108 of the cable management device 102, as shown in a first cross-section 300 in FIG. 3 and a second cross-section 400 in FIG. 4.

Figure 2:
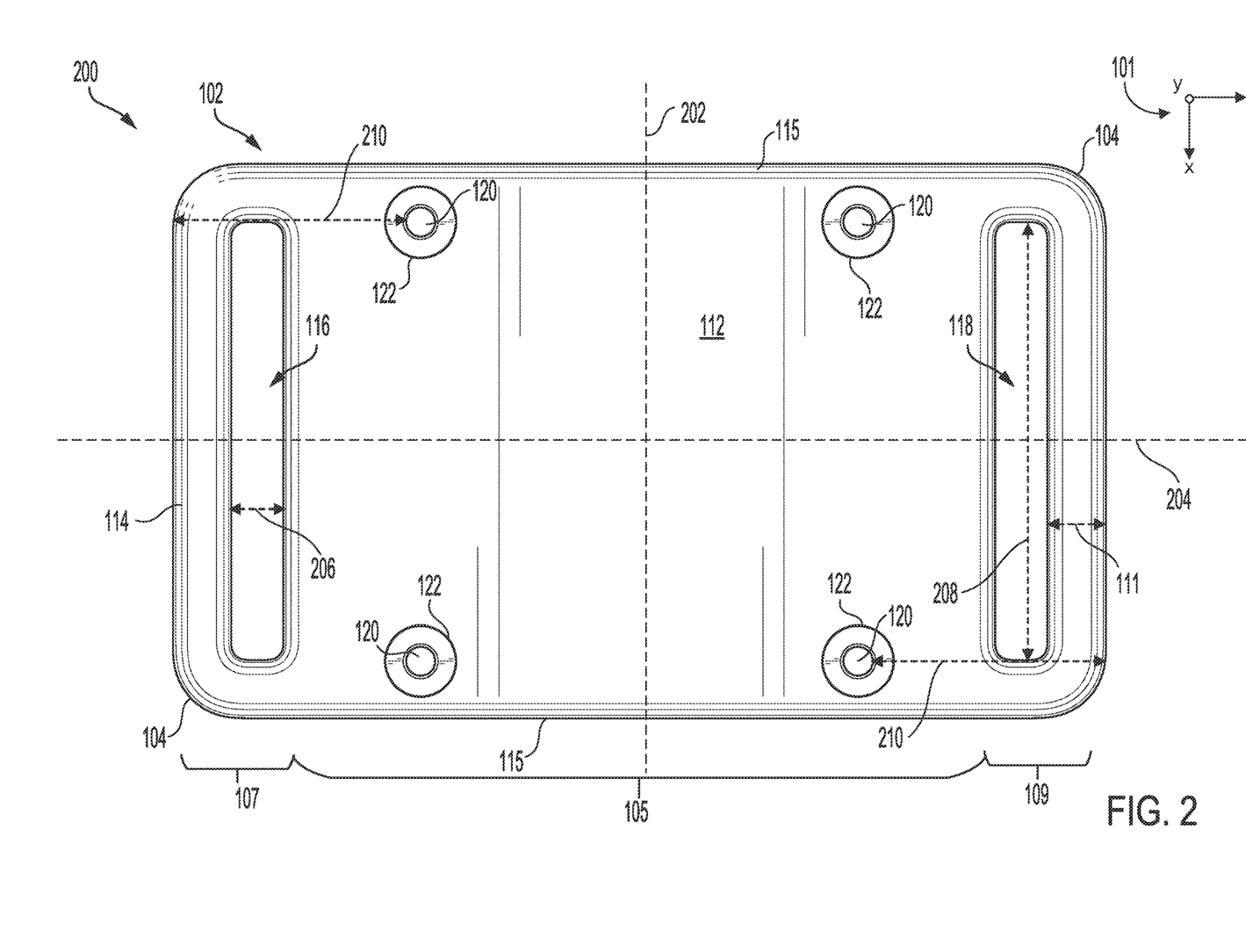
FIG. 2 shows a front view of the flexible cable management device of FIG. 1 in the first configuration.

As shown in FIG. 2 in a top view 200 of the cable management device 102, the cable management device 102 may be symmetric about a first plane 202, parallel with the x-y plane, and symmetric about a second plane 204, parallel with the y-z plane. A top face 112 of the cable management device 102 may be similar to a bottom face 302 (as shown in FIGS. 3 and 4). The top face 112 and the bottom face 302 may be parallel to one another and planar when in the first configuration.

A first set of side edges 114 and a second set of side edges 115 extend around a circumference of the cable management device 102 and between the top face 112 and bottom face 302 along the y-axis. The first set of side edges 114 are aligned with the x-axis and the second set of side edges 115 are aligned with the z-axis. The second set of side edges 115 may be longer than the first set of side edges. As shown in FIGS. 3 and 4, the first and second sets of side edges 114, 115 curve outwards, away from a central axis 103 of the cable management device 102. As such, the cable management device 102 may not have any sharp or perpendicular edges, having only smooth and continuous surfaces where intersecting regions between faces and edges of the cable management device 102 are curved.

The cable management device 102 may include a first slot 116 and second slot 118, as shown in FIGS. 1 and 2, each of the first slot 116 and the second slot 118 framed and surrounded by a first wing 107 and a second wing 109, respectively, of the cable management device 102. The wings may oppositely arranged sections of the cable management device 102 which may be mirror-images across the first plane 202 and spaced apart from one another by a central region, or base 105 of the cable management device 102. An area of the base is indicated by dashed region 230.

For example, the first wing 107 may be formed of a first strip 220, parallel with the x-axis and distal to the base 105, and a second strip 222, parallel with the first strip 220 and adjacent to the base 105. The first strip 220 is separated from the second strip 222, e.g., spaced away from the first strip 220 by the first slot 116 and coupled to the second strip 222 by arms 224 arranged perpendicular to the first strip 220 and extending between ends of the first and second strips 220, 222. The second wing 109 may be similarly configured to the first wing 107.

In one example, a width 226 of the first strip 220 may be similar to a width 228 of the arms 224 while a width 230 of the second strip 222 may be wider than the first strip 220. However, in other examples, the relative widths may vary. The first wing 107 and the second wing 109 may form opposite ends of the cable management device 102, relative to the length 106 of the cable management device 102, each of the wings arranged peripheral to the base 105 of the cable management device 102.

A sum of portions of the length 106 of the cable management device 102 forming the first and second wings 107, 109 may be less than a portion of the length 106 forming the base 105. As depicted in FIG. 2, the first slot 116 and the second slot 118 are similarly shaped and sized, each having a length 206, defined along the z-axis, that is smaller than a width 208, defined along the x-axis, of the slots. The top view 200 of FIG. 2 shows that the first slot 116 and the second slot 118 are both rectangular spaces, elongated in the direction of the x-axis, with curved corners. Further details of the first and second slots 116, 118 are shown in the first cross-section 300 of FIG. 3.

The first-cross section 300 is taken along line A-A' shown in FIG. 1, cutting the cable management device 102 in half along the y-z plane. Inner edges 304 of the first slot 116 are similarly curved as the first set of side edges 114 of the cable management device 102. The inner edges 304 curve into the first slot 116 and towards one another. In one example, a radius of curvature of the inner edges 304 may be similar to a radius of curvature of the first set of side edges 114. The second slot 118 also has curved inner edges 306 that curve towards one another, into the second slot 118. A radius of curvature of the inner edges 306 of the second slot 118 may be similar to the radii of curvature of the inner edges 304 of the first slot 116 as well as the first set of side edges 114.

The length 206 of each of the first and second slots 116, 118 may be similar to the width 111 of each of the first wing 107 and the second wing 109. In other examples, however, the length 206 of each of the slots may be greater or less than the width 111 of each of the wings. Furthermore, the length 206 of each of the slots may differ relative to the length 106 of the cable management device 102. In some examples, the lengths of the first and second slots 116, 118 may not be the same.

The second cross-section 400 shown in FIG. 4 is taken along line B-B' indicated in FIG. 1. The cable management device 102 is cut along the x-y plane through two of a plurality of mounting holes 120 disposed in the base 105 of the cable management device 102. The plurality of mounting holes 120 extend entirely through the thickness 110 of the cable management device 102 and are positioned proximate to the second set of side edges 115 within the base 105 of the cable management device 102. As shown in FIG. 2, each of the plurality of mounting holes 120 are similarly spaced away from one edge of the first set of side edges 114 by a distance 210. Each of the plurality of mounting holes 120 is aligned with one other hole of the plurality of mounting holes 120 along the x-axis and one other hole along the z-axis.

In the second cross-section 400 of FIG. 4, each of the plurality of mounting holes 120 is spaced away from one edge of the second set of edges 115 by a distance 402 which is smaller than the distance 210 (as shown in FIG. 2) that the plurality of mounting holes 120 are spaced away from the first set of side edges 114. A diameter 404 of each hole of the plurality of mounting holes 120 may be uniform through most of the thickness 110 of the cable management device 102 but may flare to become wider at the top face 112 and at the bottom face 302 of the cable management device 102.

The plurality of mounting holes 120 may be disposed in the cable management device according to dimensions of a VESA mount and configured to receive fastening devices such as screws or bolts. Thus the diameter 404 may be set, e.g., during fabrication of the cable management device, to accommodate a diameter of a type of fastener to be used to couple the cable management device to an external object or structure. The cable management device 102 may be formed of a flexible, compressible, and durable material, such as silicone or rubber, which allows the cable management device 102 to deform when a mechanical force is applied to the device and return to the first configuration shown in FIGS. 1-4 when the force is removed.

The plurality of mounting holes 120 may be reinforced with slugs 122, formed of a more rigid and less compressible material than the cable management device. For example, the slugs 122 may be formed from a plastic, a composite material, a resin, etc. The slugs 122 may be tubes circumferentially surrounding each of the plurality of mounting holes 120 that extend through the thickness 110 of the cable management device 102. As illustrated in FIG. 4, the slugs 122 have a uniform width 406 around the plurality of mounting holes 120 along the y-axis. Top surfaces 408 of the slugs 122 are co-planar and flush with the top face 112 of the cable management device 102 and bottom surfaces 410 of the slugs 122 are co-planar and flush with the bottom face 302 of the cable management device.

The slugs 122 aid in securing the cable management device 102 to a structure or object by providing rigid support to the fastening devices inserted through the plurality of mounting holes 120. For example, as shown in FIG. 8 in a perspective view 800 of a rear side of a display device 802, the cable management device 102 may be sandwiched between a rear surface 804 of the display device 802 and a plate 806 of a support arm 808. The plate 806 may enable coupling of the display device 802 to the arm 808. The plate 806, and the cable management device 102, and the display device 802 may be secured to one another by inserting upper fasteners 810 and lower fasteners 811 through upper apertures 812 and lower apertures 818, respectively, of the plate 806.

For example, the fasteners may be inserted through the plurality of mounting holes 120 of the cable management device 102 (as shown in FIGS. 1-2 and 4), and through receiving apertures in the rear surface 804 of the display device 802. The upper apertures 812, the plurality of mounting holes 120, and the receiving apertures in the rear surface 804 of the display device 802 are aligned along the y-axis and may, in one example, conform to spacing of a VESA mount.

The upper fasteners 810 and lower fasteners 811 may be, for example, threaded screws configured to engage with threading in the receiving apertures in the rear surface 804 of the display device 802. The cable management device 102 may be attached to the rear surface 804 of the display device 802 prior to engagement with the plate 806 by inserting and tightening the upper fasteners 810. As the upper fasteners 810 engage with corresponding mounting holes in the cable management device 102 and apertures in the display device 802, the upper fasteners 810 may be tightened by rotating the upper fasteners 810 with a tool, e.g., a screwdriver. Tightening the upper fasteners 810 may result in localized compression of the cable management device 102 along an upper region of the cable management device 102, with respect to the x-axis.

The rigidity of the slugs 122 (as shown in FIGS. 1-2 and 4) around the plurality of mounting holes 120 of the cable management device 102, however, resists a compressive force imposed on the slugs 122 by tightening the upper fasteners 810. The rigidity of the slugs 122 may also impede continued insertion of the upper fasteners 810 into the plurality of mounting holes 120 of the cable management device 102 beyond terminal ends of the threading of the upper fasteners 810, the terminal ends of the threading arranged at intersections of threaded regions of the upper fasteners 810 with heads of the upper fasteners 810. As a result, the fastener heads may protrude from the cable management device.

For example, a second example of a cable management device 502 is shown in FIG. 5 in a second configuration. In some examples, the cable management device 502 may be the cable management device 102 of FIGS. 1-4 and 8. The cable management device 502 is depicted from a profile view 500 in FIG. 5 and shows fastener heads 504 extending upwards, along the y-axis, from an upper face 506 of the cable management device 502. In one example, the fastener heads 504 may be non-limiting examples of the heads of the upper fasteners 810 and the lower fasteners 811 shown in FIG. 8. The fastener heads 504 may be wider in diameter 501 than the plurality of mounting holes, e.g., the plurality of mounting holes 120 of FIGS. 1-2 and 4, and therefore may protrude from the cable management device 502.

Returning to FIG. 8, the protrusion of heads of the fasteners from the surface of the cable management device 102 and the change in diameter of the fastener heads, e.g., the diameter 501 shown in FIG. 5, may be leveraged to couple the display device 802 to the plate 806. For example, the upper fasteners 810 may engage with the upper apertures 812 of the plate 806. The upper apertures 812 may be slots extending down, along the x-axis, from a top edge 816 of the plate 806, and may have a width, defined along the z-axis, that is narrower than the diameter of the heads of the upper fasteners 810.

With the cable management device 102 coupled to the rear surface 804 of the display device 802 via the upper fasteners 810, the upper fasteners 810 may be engaged with the upper apertures 812 of the plate 806 by sliding the heads of the upper fasteners 810 through the upper apertures 812. As a result, the plate 806 is in face-sharing contact with the cable management device 102 at an upper region of the plate 806, relative to the x-axis, when the heads of the upper fasteners 810 are engaged with the upper apertures 812 of the plate 806.

The plate 806 may be locked in place with respect to the cable management device 102 and the display device 802 by inserting and tightening the lower fasteners 811. The lower fasteners 811 may be inserted through the lower apertures 818 of the plate 806 and into corresponding mounting holes in the cable management device 102 and receiving apertures in the rear surface 804 of the display device 802 and tightened by rotating the lower fasteners 811.

As described above, the plurality of mounting holes 120 of the cable management device 102 are surrounded by the slugs 122, as shown in FIGS. 1, 2, and 4. The lower compressibility of the slugs 122 relative to the material of the cable management device 102 stabilizes the cable management device 102 so that wiggling and shifting of the cable management device 102 is reduced when the cable management device 102 and the rear surface 804 of the display device 802 are coupled to the plate 806 via the upper and lower fasteners 810, 811.

It will be appreciated that the engagement of the upper and lower fasteners with the apertures of the plate 806 is a non-limiting example of how the cable management device 102 and the display device 802 may be coupled to the support arm 808. Other examples may include variations in the spacing and positioning of the plurality of mounting holes 120 of the cable management 102 and the apertures in the rear surface 804 of the display device 802 (e.g., not conforming to the VESA mount). Additionally, the support arm 808 may be coupled to the display device 802 via other alternative methods. For example, the support arm 808 may be adapted to engage with the display device through a clamp, a bracket, a single fastener, etc., without departing from the scope of the present disclosure. Furthermore, the cable management device 102 may be attached to the rear surface 804 of the display device 802 through a different mechanism, such as hook-and-loop fastening tape, adhesive, etc.

When the cable management device 102 is coupled to the plate 806, the first wing 107 and the second wing 109 of the cable management device 102 may protrude along the z-axis from side edges 820 of the plate, where the side edges 820 are parallel with the x-axis. The first wing 107 and the second wing 109 of the cable management device 102 are not attached to the rear surface 804 of the display device 802 and are thus free to bend away from the rear surface 804 of the display device 802.

Bending of the first wing 107 and the second wing 109 as well as deformation of the first slot 116 and the second slot 118 may occur when cables 822 are threaded through at least one of the slots. More specifically, when plugs of the cables 822 are passed through the first slot 116 and/or the second slot 118, the first wing 107 and/or the second wing 109 may flex, allow one or more of the slots to expand and accommodate passage of the plugs.

The cables 822 may extend from one or more accessory devices, such as probes, input devices, etc., positioned adjacent to the display device 802, to a system controller or to a power supply (not shown). In some examples, a cable 824 of the display device 802 coupling the display device 802 to the system controller or the power supply may be fed through the first slot 116 (not shown in FIG. 8). The cables 822 are inserted through the second slot 118, positioned within the second slot 118 stacked along the x-axis. The length 206 of the second slot 118 may be similar to a diameter of each of the cables 822, inhibiting positioning of the cables 822 adjacent to one another along the z-axis.

By passing the cables 822 through the second slot 118 of the cable management device 102, the cables 822 may be trapped along the rear surface 804 of the display device 802 instead of draping the cables 822 over the arm 808 or other adjacent structures. The cables 822 are thus maintained along the rear surface 804 even when the display device 802 is coupled to the arm 808 and allowed to tilt, pivot, and swivel. A position of the cables 822 is retained even when the display device 802 (and the cable management device 102 attached to the rear surface 804 thereof) is detached from the plate 806 of the arm 808. In other words, the cables 822 do not fall and become distanced from the display device 802 when the display device 802 is uncoupled from the arm 808. Furthermore, the cables 822 are maintained adjacent to joints of the arm 808, the joints configured to enable movement of the arm 808 and the display device 802. By positioning the cables 822 close to the joints, movements of the arm and the display device 802 are propagated to the cables without becoming more pronounced.

The display device 802 may be attached to the arm 808 via a first joint, or a locking mechanism 826 adapted to couple the plate 806 to the arm 808. The locking mechanism 826 also enables tilting of the display device 802 through the y-x plane as indicated by arrow 830. The arm 808 may also include a second joint 828 that enables rotational movement of the display device 802. For example, the joint 828 may allow the display device to rotate along the y-z plane as indicated by arrow 832. The arm 808 may have additional joints to enable pivoting or rotating of the display device 802 through the x-z plane.

As the display device 802 is rotated, pivoted, and/or tilted, movement of the display device 802 may also cause the cables 822 to shift and twist. The cables 822 may exert a force on the cable management device 102 as the cables 822 are compelled to move and the exerted force may cause the second slot 118, and the wing 107 in which the second slot 118 is disposed, to deform. The first wing 107 and the second wing 109 may deform and flex in various ways due to a contact force exerted on the wings by the cables 822. The contact force may be a mechanically imposed pressure pushing against a portion of the wings.

For example, as shown in FIG. 5, the second example of the cable management device 502 may be adjusted to the second configuration where wings 508, similarly configured to the first and second wings 107, 109 of FIGS. 1-2 and 8, of the cable management device 502 are bent upwards in the direction of the y-axis. The wings 508, which may frame slots through which cables are inserted, may bend so that outer edges 510 of the wings 508 are higher along the y-axis than a base 512 of the cable management device 502. The bending of the wings 508 may be symmetric about a central axis 514 of the cable management device 502 and the bending may be driven by movement of the cables when cables are retained in the slots of the wings 508.

In other examples, the wings 508 may bend similarly downwards in the direction of the y-axis instead of upwards as shown in FIG. 5. In yet another example, a cable management device may deform and flex asymmetrically. For example, as shown in a profile view 600 of a third example of a cable management device 602, the cable management device 602 may have a first wing 604 and a second wing 606. The cable management device 602 is shown in an asymmetric third configuration. The first wing 604 may be flat and aligned with a base 608 of the cable management device 602 along the x-z plane. The second wing 606, however, may be bent relative to the x-z plane.

The second wing 606 may curve upwards along the y-axis, as shown in FIG. 6 or may curve downwards. The cable management device 602 is not symmetric about a central axis 610 of the cable management device 602. For example, the first wing 604 may be planar as shown in FIG. 6 or may curve in an opposite direction from the second wing 606 (as indicated in dashed lines). Thus then the second wing 606 is bent upwards, the first wing 604 may remain planar, as in the first configuration, or bend downwards. Alternatively, when the second wing 606 curves downwards, the first wing 604 may curve upwards or remain planar. Furthermore, the second wing 606 may instead be planar while the first wing 604 bends up or down along the y-axis.

A cable management device may further flex and stretch along a plane of the cable management device. As shown in a top view 700 in FIG. 7, a cable management device 702 may be similar to the cable management device 102 of FIGS. 1-4, the cable management device 502 of FIG. 5 and the cable management device 602 of FIG. 6, having a base 704, a first wing 706 surrounding a first slot 708 and a second wing 710 surrounding a second slot 712. The cable management device 702 is shown in a fourth configuration. The first slot 708 may enclose a first cable 730, with a first diameter 732 that is similar to a width 703 of the first slot 708, as well as a second cable 734 with a similar diameter to the first cable 730. The first slot 708 has a similar geometry to the first and second slots 116, 118 of FIGS. 1 and 2, e.g., when the cable management device is in the first configuration. As such, the first slot 708 is rectangular with straight sides and curved corners and has a plane of symmetry along the x-axis.

Furthermore, a similarity in diameters of the first and second cables 730, 734 to the width 703 of the first slot 708, along with a rigidity of a material of the cable management device 702, forces the first and second cables to remain aligned along the x-axis. The cables may remain stacked along the x-axis even when the cable shifts and rotate due to a resistance of the cable management device material to cable movement. However, the material provides sufficient elasticity to stretch and flex to allow the cables to turn and/or shift in any direction without binding or chafing the cables.

The second slot 712 is not rectangular. Instead, the second slot 712 has a shape resembling the letter "D". In other words, when the second slot 712 is D-shaped, the second slot 712 has a straight edge with opposite ends of the straight side coupled to opposite ends of a curve or arc. The second wing 710 is distended away from the base 704 of the cable management device 702 along a long section (e.g., a section extending along x-axis) of the second wing 710 so that the second slot 712 does not have a plane of symmetry along the x-axis. The second slot 712 may be deformed due to insertion of a head of a cable, e.g., a plug 705, which may have a greater width 724 than a width of the second slot 712 when the second slot 712 is not stretched, e.g., the width 703 of the first slot 708.

The plug 705 may be a rigid structure that, when inserted between a first inner edge 716 and a second inner edge 722 of the second slot 712, may exert a force on the first inner edge 716 along a direction indicated by arrows 718 and on the second inner edge 722 along an opposite direction indicated by arrows 707. The second inner edge 722 resists the force due to an amount material forming the base 704 compared to an amount of material forming the second wing 710 as well as a coupling of the base 704 to an external structure, such as the display device 802 of FIG. 8.

At portions of the first inner edge 716 and the second inner edge 722 in direct contact with the plug 705, the distance between the first inner edge 716 and the second inner edge 722 increases to become similar to the width 724 of the plug 705. However, the second inner edge 722 remains unaltered and linear and only the first inner edge 716 is stretched to accommodate a size of the plug 705.

The plug 705 may be pushed through the second slot 712 so that the plug 705 passes entirely through the second slot 712 and a second cable 720, to which the plug 705 is coupled, may instead be enclosed in the second slot 712. The second cable 720 may have a diameter similar to the width 703 of the first slot 708, removing the forces exerted along the first inner edge 716 and the second inner edge 722 as indicated by arrows 718 and 707. The second wing 710 may rebound and return to a rectangular shape, as indicated by dashed line 726, and resemble a shape of the first wing 706 with a plane of symmetry along the x-axis.

In some examples, the second wing 710 may be deformed into the D-shaped geometry of the fourth configuration due to a contact force exerted by the second cable 720. For example, when the second cable 720 is pulled with sufficient tension in the direction indicated by arrows 718, the first inner edge 716 of the second slot 712 may also be forced to curve away from the second inner edge 722. In other examples, the second wing 710 may be flexed in into the fourth configuration by some other type of object, such as an operator's hand, a current converter coupled to the second cable 720, etc.

As described above, when the second slot 712 is deformed into the D-shaped geometry due to a contact force imposed by either the plug 705, the second cable 720, or some other object, the increased distance between the first inner edge 716 and the second inner edge 722 increases an inner volume of the second slot 712 compared to when the plug 705 is not inserted, e.g., as indicated by dashed line 726. For example, the distance between the first inner edge 716 and the second inner edge 722 may increase by up to three times the distance when opened or when the plug 705 is inserted.

The slots of the cable management device may alternate between the symmetric rectangular geometry shown by the first slot 708 and the D-shaped geometry of the second slot 712, shown in FIG. 7. It will be appreciated that the first slot 708 may also conform to the D-shaped geometry concurrent with the second slot 712 when at least one plug is also pushed through the first slot 708. Furthermore, an amount that the wings distend and curve away from the base of the cable management device 702 may vary depending on a size of the object inserted therethrough or a magnitude of the force exerted by the object.

The fourth configuration of the cable management device may be combined with the second and third configurations of FIGS. 5 and 6 respectively. For example, one or both of the slots of the cable management device may be adjusted to the D-shaped geometry by plugs extending through the slots while the one or both of the wings may be forced to curve and bend in a direction perpendicular to the plane of the cable management device. The wings may bend in a same direction or in opposite directions.

When the plugs are passed entirely through the slots, the cable management device may be rebound to the first configuration while retaining the cables. The flexibility of the material of the cable management device allows the wings of the cable management device to stretch by small amounts, thereby maintaining an amount of pressure exerted on the cables by the inner edges of the slots below a threshold level that may otherwise degrade the cables. Additionally, by implementing the inner edges of the slots with curved surfaces extending between the planar faces of the cable management device and maintaining the cables stacked within the slot, a likelihood of chafing of the cables is reduced.

In this way, the cable management device may be readily mounted to a display device, as shown in FIG. 8, as a unitary structure and maintained in a location of the display device that does not affect operation of the display device or accessory devices. The slots of the cable management device are configured to receive cable heads (e.g., plugs) and retain cables of the display device and accessory devices once the plugs are passed through the slots. The cable management device enables organized securing of the cables so that the cables do not become tangled or interfere with access to the display device or accessory devices.

By forming the cable management device from a flexible, elastic, rebounding material such as silicone or rubber, the cable management device may stretch, bend and flex in response to insertion of plugs through slots of the cable management device. Furthermore, shifting of the cables may occur during, for example, operation of the accessory devices or during tilting/rotating of the display device. As the cables move, the cable may rotate and twist and the slots of the cable management device may flex to accommodate the movement while maintaining a stacking of the cables within the slots along a width of the cable management device. The flexing of the cable management device may also circumvent pulling of the cables which may otherwise cause the cables to become unplugged. Binding, crimping and chafing of the cables is circumvented.

The cable management device may be formed by a low cost method of fabrication, such as 3-D printing, injection molding, etc. The material of the cable management device may have a hardness/flexibility commensurate with a stiffness of the cables. For example, a cable management device with a higher durometer value may be used with stiffer cables than a cable management device with a lower durometer value. The cable management device may be easily modified to include more than two slots, slots of different sizes and shapes, etc. In other examples, the cable management device may be implemented in a perpendicular orientation when mounted to the display device than that shown in FIG. 8 so that the slots of the cable management device are positioned above and below the plate 806 coupling the display device 802 to the arm 808.

A method 900 for organizing cables of a medical system using a cable management device is shown in FIG. 9. The cable management device may be the cable management device 102 of FIGS. 1-4 and 8, 502 of FIG. 5, 602 of FIG. 6, or 702 of FIG. 7. As such, the cable management device may have a plurality of holes disposed in a base of the cable management device according to spacing of a VESA mount. At least one slot is included in the cable management device and configured to receive one or more cables. For example, the cable management device may have two slots arranged at opposite ends of the cable management device in wings of the cable management device that remain unanchored and able to bend and stretched.

At 902, the method includes attaching the cable management device to a display device of a medical system. The display device may be a monitor, for example, and the cable management device may be coupled to a rear surface of the display device by aligning the plurality of holes of the cable management device with apertures in the rear surface of the display device. Threaded upper fasteners, adapted to extend through upper holes of the plurality of holes and engage with threaded upper apertures in the rear surface of the display device, may be inserted through the upper holes and tightened within the upper apertures by rotating the upper fasteners.

The display device may be coupled to a support arm at a plate of the support arm, e.g., the plate 806 of FIG. 8. The plate may have a set of upper slots and a set of lower apertures, as shown in FIG. 8, and the upper fasteners may engage with the set of upper slots by sliding heads of the upper fasteners through the set of upper slots. The heads of the upper fasteners may protrude outwards from a surface of the cable management device due to a wider diameter of the heads than a diameter of the threaded upper apertures in the rear surface of the display device. Furthermore, the diameter of the heads may taper to increase at a top of the heads, as shown in FIGS. 5 and 6.

A width of each of the set of upper slots may be similar to a narrow region of the heads, e.g., a region of the heads proximate to the surface of the cable management device. Thus, when the heads of the upper fasteners are inserted into the set of upper slots and the display device slid downwards until the heads abut terminal ends of the set of upper slots, the cable management device may be in face-sharing contact with a surface of the plate and sandwiched between the plate and the rear surface of the display device.

At 904, the display device may be secured to the support arm, e.g., fastened to the plate of the support arm, by inserting lower threaded fasteners through the set of lower apertures in the plate, through lower holes of the plurality of holes of the cable management device, and into lower threaded apertures in the rear surface of the display device. The lower threaded fasteners may be tightened in the lower threaded apertures of the rear surface of the display device by rotating the lower threaded fasteners. As the lower threaded fasteners are tightened, the cable management device may be compressed between the plate and the rear surface of the display device so that there are no spaces between the surfaces.

In some examples, compression of the cable management device may be resisted by slugs, formed of a more rigid and less compressible material than the cable management device, surrounding each of the plurality of apertures. The slugs enable the cable management device to be fastened securely to the support arm and the display area without shifting and excessive compression of the base of the cable management device that may otherwise lead to undesirable deformation.

While the base of the cable management device is secured to the plate and the rear surface of the display device, the wings of the cable management device are not similarly secured. Instead the wings protrude from sides of the plate of the supporting arm, allowing the wings to bend and stretch when a force is exerted on the wings.

At 906, the method includes feeding cables of the display device and/or accessory devices of the medical system through the slots of the cable management device. The cables may have plugs coupled to terminal ends of the plugs where the plugs are wider than a diameter of the cables. Thus feeding the cables through the slots may first include pushing the plugs through the slots. The cable management may initially be in the first configuration shown in FIGS. 1-4 and upon inserting the plugs, may be adjusted to the fourth configuration shown in FIG. 7, for example. The cable management may further be adjusted into the second configuration shown in FIG. 5 or the third configuration shown in FIG. 6 in combination with the fourth configuration. When the plugs are passed through the slots and the cables are instead fed through the slots, the slots return to the first configuration of the cable management device, thereby retaining the cables at the rear side of the display device.

In this way, cables of a medical system may be maintained at a rear side of the medical system, away from an operator. The cables may be coupled to a cable management device attached to a rear surface of a display device of the medical system, proximate to an arm supporting the display device and configured to be mobile. As the arm tilts, pivots, and/or rotates, the movement of the arm may cause the cables to slide and twist. By forming the cable management device from a flexible, elastic, rebounding material, the cable management device may stretch and bend to accommodate movement of the cables, thereby reducing a likelihood of binding and chafing of the cables. The cable management device may be a unitary structure with continuous surfaces, allowing the cable management device to be easily sanitized.

The technical effect of implementing the medical system with the cable management device is that strain on the cables arising from contact of the cables with sharp and rigid structures is reduced.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

In one embodiment, a cable management device includes a planar base with a plurality of mounting holes, a first wing framing a first slot positioned along a first side of the base and a second wing framing a second slot positioned along a second side of the base, opposite of the first side, and wherein the first wing and the second wing are configured to flex from a first configuration to a second configuration in response to a contact force exerted on the wings. In a first example of the cable management device, the cable management device is a single, unitary structure with curved edges extending between planar surfaces of the cable management device. A second example of the cable management device optionally includes the first example, and further includes, wherein each of the first slot and the second slot has a first inner edge distal to the base and a second inner edge proximate to the base and wherein the first configuration includes a parallel and linear alignment of the first inner edge with the second inner edge. A third example of the cable management device optionally includes one or more of the first and second examples, and further includes, wherein the second configuration is a receiving position configured to receive an object exerting the contact force on at least one of the first and second wings and wherein when in the second configuration, the first inner edge of at least one of the first and second slots is flexed to curve away from the second inner edge so that a distance between the first and second inner edge increases relative to the first configuration. A fourth example of the cable management device optionally includes one or more of the first through third examples, and further includes, a third configuration where at least one of the first wing and/or the second wing is bent and not co-planar with the base of the cable management device and wherein the cable management device is in the third configuration concurrent with the second configuration. A fifth example of the cable management device optionally includes one or more of the first through fourth examples, and further includes, wherein the second inner edge of each slot remains linear and unchanged when the contact force is exerted on at least one of the first inner edge or the second inner edge of each slot. A sixth example of the cable management device optionally includes one or more of the first through fifth examples, and further includes, wherein the first and second slots rebound from the second configuration to the first configuration when the contact force is removed.

In another embodiment, a cable management system includes a display device with receiving apertures disposed in a rear surface of the display device and configured to couple to a support arm, and an elastic, flexible panel positioned between the display device and the support arm, the panel having a central base region with a plurality of mounting holes with a spacing of the plurality of mounting holes matching a spacing of the receiving apertures of the display device, and wherein the panel includes wings arranged on opposite sides of the base region, each of the wings framing a retention slot. In a first example of the cable management system, cables are maintained along the rear surface of the display device when inserted through at least one of the retention slots and a position of the cables along the rear surface is retained when the display device is decoupled from the support arm. A second example of the cable management system optionally includes the first example, and further includes, wherein the panel is mounted to the rear surface of the display device by fasteners inserted into the plurality of mounting holes and extending into the receiving apertures in the rear surface of the display device. A third example of the cable management system optionally includes one or more of the first and second examples and further includes, wherein the base of the panel is maintained in a planar configuration when the fasteners are inserted and the base is coupled to the rear surface of the display device and wherein the wings of the panel are not attached to the rear surface of the display device. A fourth example of the cable management system optionally includes one or more of the first through third examples and further includes a first configuration of the panel when the cables are inserted through at least one retention slot of the first wing and/or the second wing and inner edges of the retention slot are parallel. A fifth example of the cable management system optionally includes one or more of the first through fourth examples, and further includes a second configuration of the panel when plugs coupled to the cables are inserted into the retention slot and wherein a width of the retention slot increases to match a width of the plugs and the inner edges of the retention slot are not parallel. A sixth example of the cable management system optionally includes one or more of the first through fifth examples, and further includes, wherein the panel is adjusted to the second configuration when the cables are inserted through at least one retention slot of the first wing and/or the second wing and the cables exert a contact force on the inner edges of the retention slot. A seventh example of the cable management system optionally includes one or more of the first through sixth examples, and further includes, wherein the first wing and the second wing bend and flex away from the rear surface of the display device when the cables exert the contact force on the inner edges of the retention slot of each of the wings. An eighth example of the cable management system optionally includes one or more of the first through seventh examples, and further includes, wherein each of the plurality of holes of the panel are surrounded by a slug formed of a more rigid and less compressible material than the base or the peripheral wings of the panel.

In yet another embodiment, a method includes coupling a flexible panel to a rear surface of a display device, the flexible panel having a set of slots arranged on opposite sides of a central base of the panel, attaching the display device and the flexible panel to an arm configured to support the display device, and feeding cables through the set of slots of the flexible panel to maintain the cables proximate to the rear surface of the display device. In a first example of the method, coupling the panel to the rear surface of the display device includes inserting a set of upper fasteners into upper mounting holes of the flexible panel and upper receiving apertures in the rear surface of the display device and wherein attaching the display device and the flexible panel to the arm includes engaging heads of the set of upper fasteners with upper apertures of a plate of the arm, the plate configured to interface with a second face of the flexible panel, the second face opposite of the first face. A second example of the method optionally includes the first example, and further includes securing an attachment of the display device to the plate of the arm by inserting a set of lower fasteners through lower apertures in the plate, lower mounting holes of the flexible panel, and lower receiving apertures in the rear surface of the display device. A third example of the method optionally includes one or more of the first and second examples and further includes, wherein feeding cables through the set of slots includes inserting plugs through the set of slots, the plugs coupled to terminal ends of the cables, while increasing the set of slots from a first width to a second width, and decreasing the set of slots from the second width to the first width when the cable plugs are outside of the set of slots and the cables are retained within the set of slots.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A cable management device comprising:
a first wing framing a first slot positioned along a first side of the cable management device and a second wing framing a second slot positioned along a second side of the cable management device, opposite of the first side; and
wherein the first wing and the second wing are configured to flex from a first configuration to a second configuration in response to a contact force exerted on the wings.

2. The cable management device of claim 1, wherein the cable management is formed of a first section and a second section, the first section and the second section separate from and mirror images of one another and wherein the first section includes the first wing and a first planar base coupled to the first wing and the second section includes the second wing and a second planar base coupled to the second wing.

3. The cable management device of claim 1, wherein the cable management device is a single, unitary structure and wherein the cable management device includes a planar base extending between the first wing and the second.

4. The cable management device of claim 1, wherein the first and second slots rebound from the second configuration to the first configuration when the contact force is removed.

5. The cable management device of claim 1, wherein each of the first slot and the second slot has a first inner edge proximate to the first wing and the second wing, respectively, and a second inner edge distal to the first wing and the second wing, respectively, and wherein the first configuration includes a parallel and linear alignment of the first inner edge with the second inner edge.

6. The cable management device of claim 5, further comprising a third configuration where at least one of the first wing and/or the second wing is bent and not co-planar with the other of the first wing and the second wing and wherein the cable management device is in the third configuration concurrent with the second configuration.

7. The cable management device of claim 5, wherein the second configuration is a receiving position configured to receive an object exerting the contact force on at least one of the first and second wings and wherein when in the second configuration, the first inner edge of at least one of the first and second slots is flexed to curve away from the second inner edge so that a distance between the first and second inner edge increases relative to the first configuration.

8. The cable management device of claim 7, wherein the second inner edge of each slot remains linear and unchanged when the contact force is exerted on at least one of the first inner edge or the second inner edge of each slot.

9. A cable management system comprising:
an apparatus with receiving apertures disposed in a rear surface of the apparatus and configured to couple to a support arm; and
an elastic, flexible device coupled to the rear surface of the apparatus, the device having a plurality of mounting holes with a spacing of the plurality of mounting holes matching a spacing of the receiving apertures of the apparatus, and wherein the device includes wings arranged on opposite sides of the device, each of the wings framing a retention slot.

10. The cable management system of claim 9, wherein the apparatus is a display device and wherein the device is fixedly coupled to the display device.

11. The cable management system of claim 9, wherein the apparatus is a cradle configured to support a display system and wherein the device is fixedly coupled to the cradle.

12. The cable management system of claim 9, wherein cables are maintained along the rear surface of the apparatus when inserted through at least one of the retention slots and a position of the cables along the rear surface is retained when the apparatus is decoupled from the support arm and wherein the wings are not attached to the rear surface of the apparatus.

13. The cable management system of claim 12, the device is a single, unitary structure with a planar base extending between the wings, the planar base including the plurality of mounting holes, and wherein the planar base is positioned between the rear surface of the apparatus and the support arm and maintained in a planar configuration, when the apparatus is coupled to the support arm.

14. The cable management system of claim 12, wherein the device is formed of two, separate sections, each section including a planar base with a portion of the plurality of mounting holes and coupled to one of the wings and wherein when the support arm is coupled to the rear surface of the apparatus, the support arm is in direct contact with the rear surface of the apparatus and the two sections of the device are positioned on opposite sides of the support arm and coupled to the rear surface of the apparatus.

15. The cable management system of claim 9, further comprising a first configuration of the device when the cables are inserted through at least one retention slot of the first wing and/or the second wing and inner edges of the retention slot are parallel and a second configuration of the device when plugs coupled to the cables are inserted into the retention slot and wherein a width of the retention slot increases to match a width of the plugs and the inner edges of the retention slot are not parallel.

16. The cable management system of claim 15, wherein the first wing and the second wing bend and flex away from the rear surface of the apparatus when the cables exert the contact force on the inner edges of the retention slot of each of the wings.

17. A method for a cable management system, comprising:
    coupling a flexible device to a rear surface of an apparatus, the flexible device having a set of slots arranged on opposite sides of the device;
    attaching the apparatus and the flexible device to an arm configured to support the apparatus; and
    feeding cables through the set of slots of the flexible device to maintain the cables proximate to the rear surface of the apparatus.

18. The method of claim 17, wherein coupling the flexible device to the rear surface of the apparatus includes securing the flexible device to a display device and wherein the flexible device is secured to the display device by inserting fasteners through corresponding apertures in the flexible device and the display device.

19. The method of claim 18, wherein coupling the flexible device to the rear surface of the apparatus includes securing the flexible device to a cradle supporting a display device and wherein the flexible device is secured to the cradle by inserting fasteners through corresponding apertures in the flexible device and the cradle.

20. The method of claim 17, wherein feeding cables through the set of slots includes inserting plugs through the set of slots, the plugs coupled to terminal ends of the cables, while increasing the set of slots from a first width to a second width, and decreasing the set of slots from the second width to the first width when the cable plugs are outside of the set of slots and the cables are retained within the set of slots.

* * * * *